(12) United States Patent  
Policker et al.

(10) Patent No.: US 6,694,192 B2
(45) Date of Patent: Feb. 17, 2004

(54) UTERUS MUSCLE CONTROLLER

(75) Inventors: Shai Policker, Moshav Zur Moshe (IL); Ricardo Aviv, Haifa (IL); Daniel Kamil, Moshav Bnei Zion (IL)

(73) Assignee: Impulse Dynamics N.V., Curacao (AN)

( * ) Notice: Subject to any disclaimer, the term of this patent is extended or adjusted under 35 U.S.C. 154(b) by 261 days.

(21) Appl. No.: 09/753,848

(22) Filed: Jan. 3, 2001

(65) Prior Publication Data

US 2002/0010494 A1 Jan. 24, 2002

Related U.S. Application Data

(60) Provisional application No. 60/216,076, filed on Jul. 6, 2000.

(51) Int. Cl.[7] .................................................. A61N 1/00
(52) U.S. Cl. ........................ 607/115; 607/41; 607/138; 600/304; 600/372; 606/193
(58) Field of Search ................................ 607/9, 39–42, 607/50, 62, 138; 600/372, 587, 561, 591, 29, 304; 604/174, 117, 66, 517, 544; 606/193

(56) References Cited

U.S. PATENT DOCUMENTS

| 4,114,188 | A | * | 9/1978 | Carter et al. ................. 600/591 |
|---|---|---|---|---|
| 5,301,680 | A | * | 4/1994 | Rosenberg ................... 600/546 |
| 5,397,344 | A | * | 3/1995 | Garfield et al. .............. 607/138 |
| 5,447,526 | A | * | 9/1995 | Karsdon ....................... 607/39 |
| 5,546,953 | A | * | 8/1996 | Garfield ....................... 600/546 |
| 5,671,749 | A | * | 9/1997 | Hon ............................. 607/902 |
| 5,713,940 | A | | 2/1998 | Karsdon |
| 5,738,096 | A | * | 4/1998 | Ben-Haim ................... 600/407 |
| 5,964,789 | A | | 10/1999 | Karsdon |
| 5,991,649 | A | * | 11/1999 | Garfield et al. .............. 600/372 |
| 6,317,631 | B1 | * | 11/2001 | Ben-Haim et al. ............ 607/9 |
| 6,421,558 | B1 | * | 7/2002 | Huey et al. .................. 600/546 |
| 2002/0052632 | A1 | * | 5/2002 | Ben-Haim et al. ............ 607/9 |
| 2002/0183686 | A1 | * | 12/2002 | Darvish et al. ............... 604/21 |

FOREIGN PATENT DOCUMENTS

| EP | 1166715 | * | 1/2002 |
|---|---|---|---|
| WO | 97/25098 | * | 7/1997 |
| WO | 99/03533 | * | 1/1999 |

OTHER PUBLICATIONS

Uterine Electromyography: A Critical Review, by D. Devedeux et al., Am. J. Obstet Gynecol 1993, 169, 1636–53.

* cited by examiner

Primary Examiner—Tu Ba Hoang
(74) Attorney, Agent, or Firm—Reed Smith LLP; William H. Dippert

(57) ABSTRACT

A method and apparatus for controlling uterine contractions in a female comprises providing sensors for sensing uterine contractions; providing an electric signal generator for generating signals to be applied on the uterus; providing a control unit for receiving signal corresponding to uterus contractions from the sensors and actuate said signal generator to generate a non-excitatory electric signal in a predetermined timing and duration with respect to a sensed uterine contraction; providing signal delivery leads for delivering the electric signal from the electric signal generator to predetermined locations on the uterus; sensing a uterine contraction using the sensors; and applying non-excitatory electric field at the predetermined locations on the uterus in predetermined timing and duration with respect to the sensed uterine contraction.

71 Claims, 11 Drawing Sheets

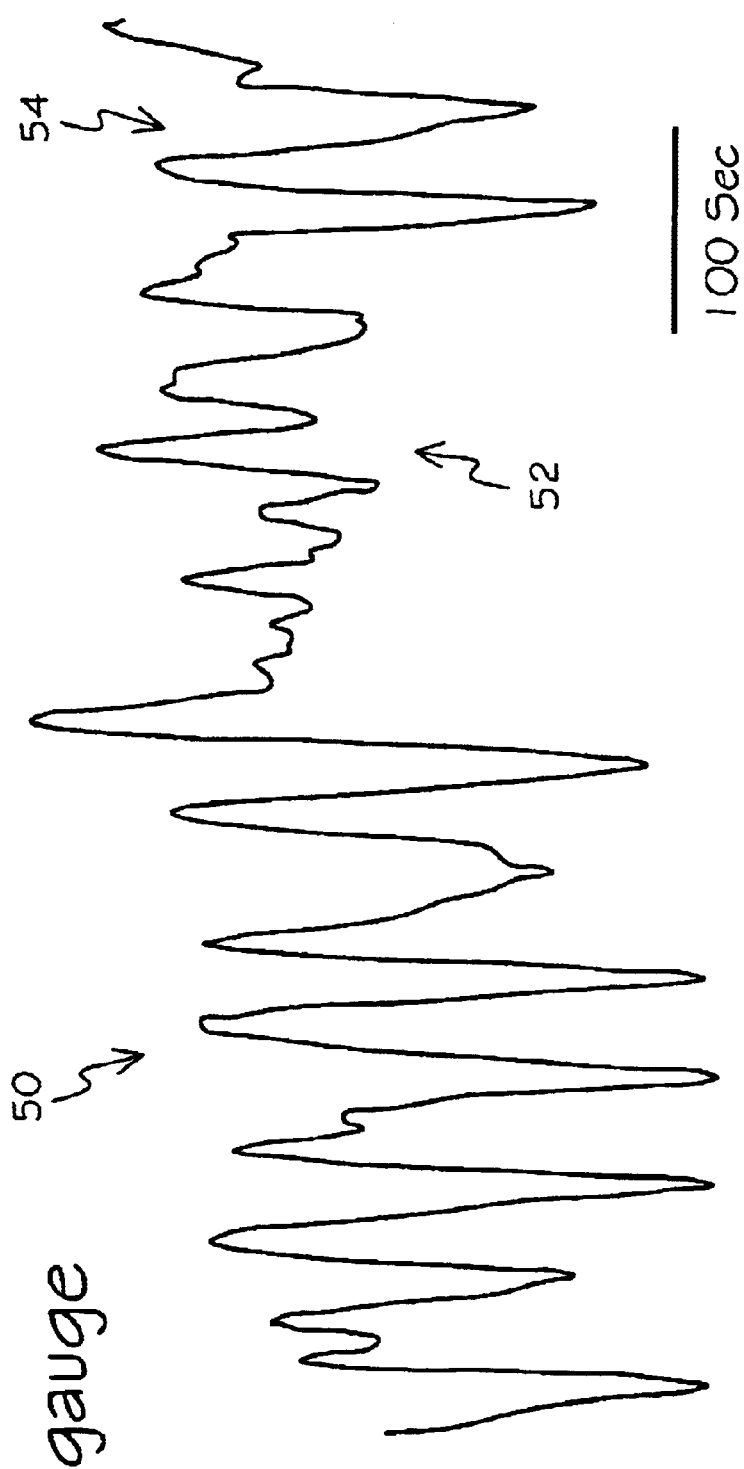

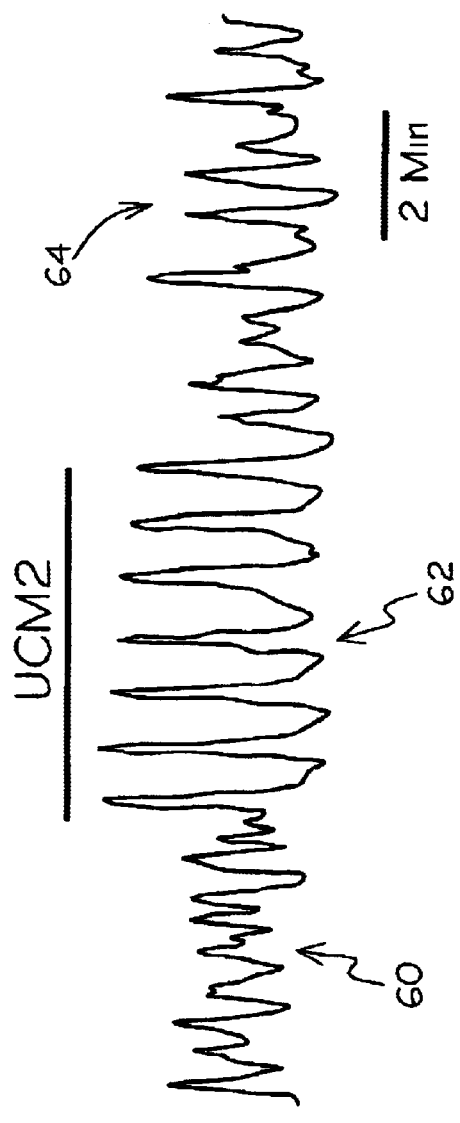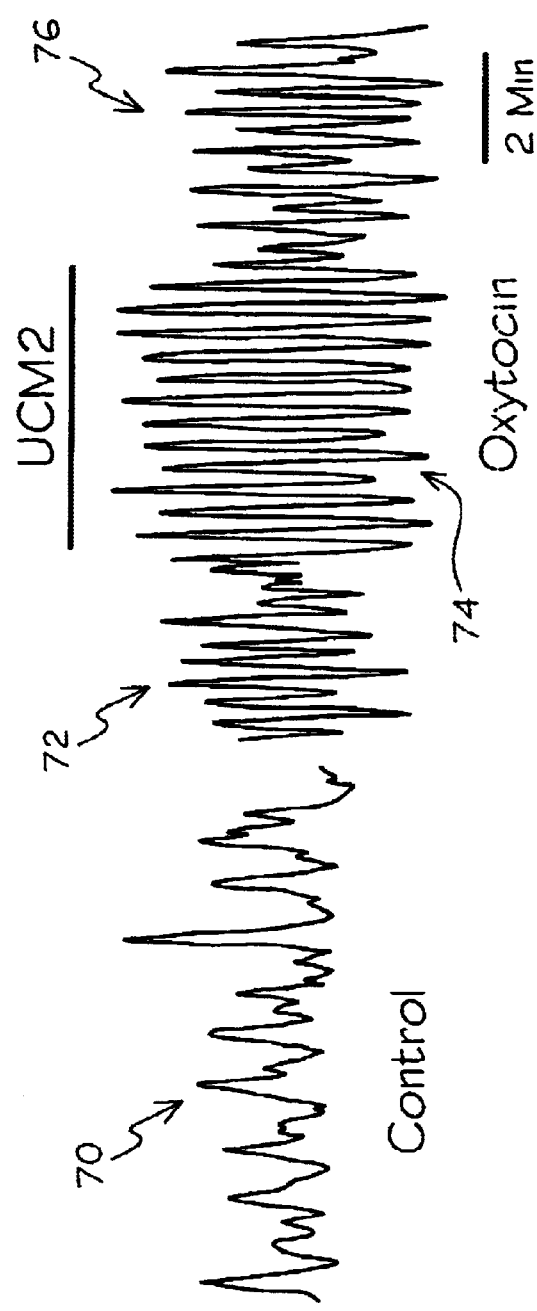
Fig. 4a
Fig. 4b

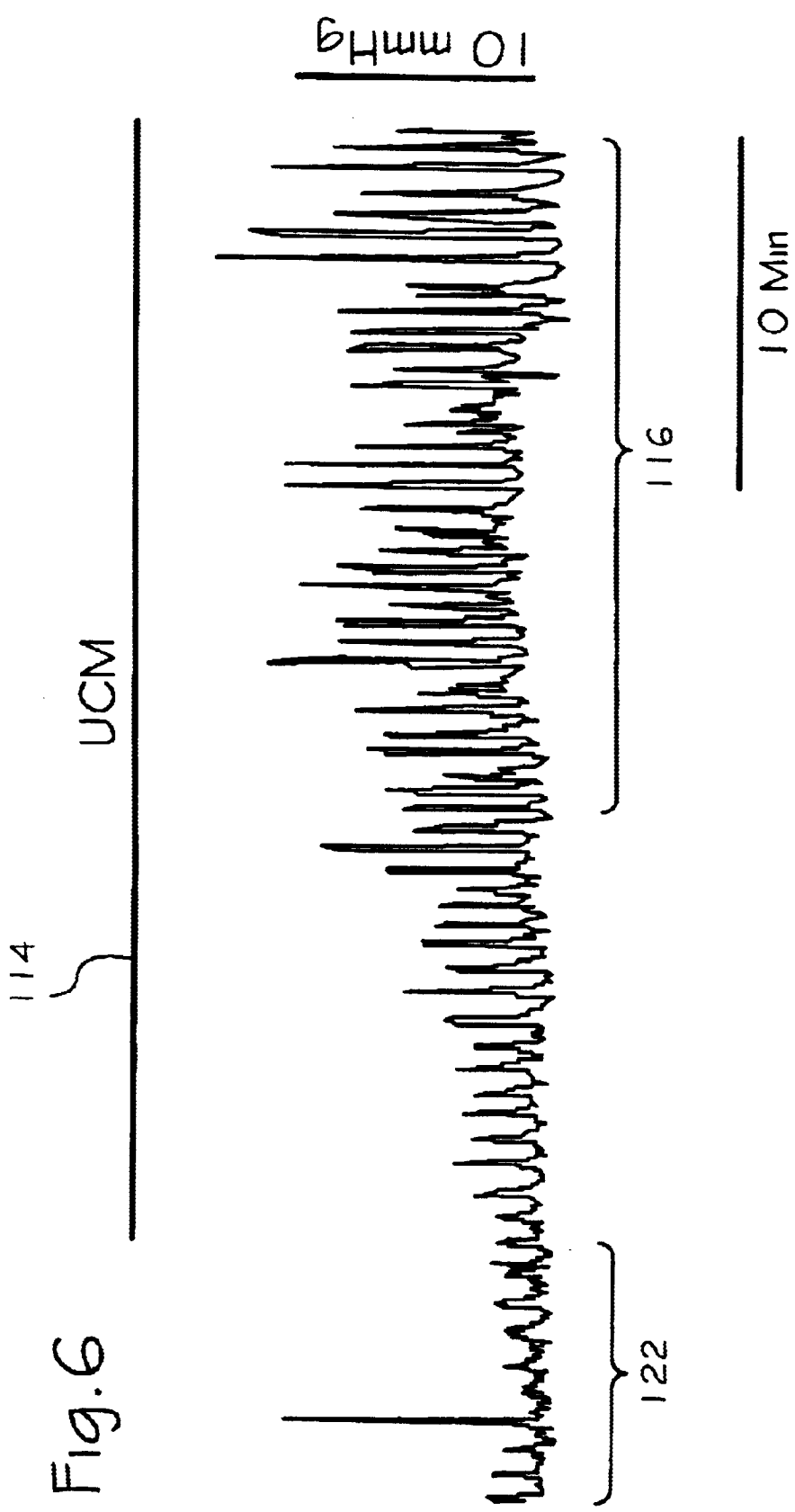

UTERUS MUSCLE CONTROLLER

The present invention relates to medical intervention and control of the uterus. More particularly it relates to electrical inhibition or enhancement of the uterus activity. This application corresponds to U.S. Provisional Patent Application Ser. No. 60/216,076, filed on Jul. 6, 2000.

FIELD OF THE INVENTION

BACKGROUND OF THE INVENTION

Preterm (or premature) labor is the second most important reason for fetal morbidity and mortality after fetal anomalies, occurring in about 10 percent of all pregnancies (8–12% of all labors in the US are premature. The total annual number of premature deliveries is about 400,000). Preterm labor is usually defined as the onset of labor before 37 weeks of pregnancy have been completed. The symptoms of preterm labor include uterine contractions at regular intervals that begin before the fetus is mature, usually before the due date of delivery, passage of bloody mucus, flow of fluid (amniotic fluid) from the uterus, that may occur with a gush or may be only a continuous watery discharge.

Main causes of preterm labor include premature rupture of the amniotic membranes ("water breaks"), illness of the mother, including pre-eclampsia, high blood pressure or diabetes, abnormal shape or size of the uterus, weak or short cervix, hormone imbalance, vaginal infection that spreads to the uterus, large fetus or more than one fetus, abnormalities of the placenta, such as placenta previa, and excessive amniotic fluid.

Tocolytic agents (medications used to inhibit labor), such as Beta-adrenergic agents, Magnesium sulfate, Prostaglandin inhibitors, Calcium channel blocker, are usually used to treat preterm labor and permit pregnancy to proceed so that the fetus can gain more size and maturity before delivery.

However, it was found that tocolytic agents are effective only in short term (up to 72 h) with efficacy of 40–50%. Moreover, they present severe adverse effects for both mother and fetus.

Cervical cerclage, on the other hand, have long term efficacy, but is a relevant therapy for only 2–4% of all preterm labor cases, and comprises surgical intervention.

Itis not always possible to inhibit labor contractions and stop the labor process by drugs. Moreover, the efficiency of drugs on the inhibition of labor is low, and is associated with many adverse effects (even cervical cerclage in small percentage of patients).

Electric muscle control is not a new concept, dating back to Galvani's experiments, applying electrical field to a dead frog's leg and causing its twitching (Galvani himself thought it to be the result of the generation of electricity in the dead animal's leg). For example, PCT/IL97/00012 (Ben-Haim et al.), published as WO 97/25098 and titled ELECTRICAL MUSCLE CONTROLLER now U.S. Pat. No. 6,363,279) described an electrical muscle controller for applying non-excitatory electric stimulation of the cardiac muscle in order to gain enhanced contractility, all incorporated herein by reference. It is noted that by "non-excitatory electric stimulation" it is meant electric stimulation that does not initiate electrical activation signal. An activation signal is an electrical signal which, when it reaches an excitable cell, causes it to depolarize and perform its destined activity.

In PCT/IL97/00243 published as WO 99/03533, titled SMOOTH MUSCLE CONTROLLER, there was described a method of directly and locally controlling the contraction and the force of contraction of smooth muscles.

The uterus muscle is also a smooth muscle that contracts in response to electrical activation signals. The uterus wall is composed of myometrium tissue, which is excitable and suitable for excitable tissue control (ETC) therapy of motion modulation through electrical non-stimulatory signal. See: "Uterine Electromyography: A Critical Review", by D. Deveduex et al., Am. J. Obstet Gynecol 1993, 169, 1636–53.

U.S. Pat. No. 5,447,526 (Karsdon), filed in 1992, titled TRANSCUTANEOUS ELECTRIC MUSCLE/NERVE CONTROLLER/FEEDBACK UNIT, described a transcutaneous device for inhibiting uterine contractions. It comprises a first plurality electrode positioned on an anterior side of an abdomen of a patient, extending laterally above an upper portion of the uterus, a second plurality electrode positioned on the anterior side of the abdomen of the patient, extending laterally on the mid to lower portion of the uterus. U.S. Pat. No. 5,964,789 (Karsdon) and U.S. Pat. No. 5,713,940 (Karsdon) describe similar versions of devices as in U.S. Pat. No. 5,447,526.

Karsdon explains that as opposed to prior art electrical control devices, which are generally aimed at stimulating or increasing muscle activity, his devices are aimed at inhibiting muscular activity. Karsdon explains that his devices employ relatively long electrical pulses with a plurality of wave patterns, and constant current output.

U.S. Pat. No. 5,991,649 (Garfield et al.), filed in 1996, titled METHODS FOR ACTIVATING THE MUSCLE CELLS OR NERVES OF THE UTERUS OR CERVIX, also described electrical control of uterus activity.

It is established that both Karsdon and Garfield suggest applying excitatory signals to the uterus (given the suggested length of the applied signals, as well as explicit mentioning—by Garfield—of the action potential propagation).

But although the concept of inhibiting labor contractions, using electrical signals, per se, is not entirely new, the present invention suggests an entirely novel approach to induction of labor using non-excitatory electrical stimulation.

Prior art methods of inducing labor included natural methods, such as rupturing the membranes, stripping the membranes during pelvic examination, nipple stimulation to release one's own natural oxytocin, administration of enema or drinking castor oil, and even just walking. Application of drugs that cause induced labor in the event of failure to commence spontaneous labor is carried out if these natural methods fail.

Commonly labor inducing drugs include oxytocin, pitocin (a synthetic form of oxytocin) given intravenously or Prostaglandin (usually in the form of gel or suppository).

Oxytocin causes prelabor contractions to increase both in amplitude and in rhythm. But although increased contraction amplitude is desirable, increased contraction rhythm may result in fetus stress. During strong contractions the fetus is pressed inside the uterus, its navel cord may be squeezed, and as a result the oxygen supply may be temporarily halted or severely reduced. In naturally rhythmic labor contractions the fetus is given enough time to recover, but if the pace of the contractions is speeded up serious irreversible damage may occur. Fetus stress can be monitored using commonly available monitoring devices (where usually the fetus heart rate as well as other parameters are tracked).

The correct dose of oxytocin is not initially known and varies from patient to patient. It depends, inter alia, on the readiness of the uterus for labor, and therefore administering over dose of oxytocin is not uncommon. Over dose of oxytocin may result in extreme cases in tearing of the uterus due to violent hypertonic contractions. As the duration of the oxytocin effect is determined by the given dose and the half life period (typically 3–5 minutes), the only way to cancel oxytocin effect before the wash-out period is by administering a tocolytic drug.

BRIEF DESCRIPTION OF THE INVENTION

The present invention seeks to provide novel method and device for inhibiting or enhancing and even initiating uterus contractions, i.e. inhibiting preterm labor or inducing or expediting labor in overdue pregnancy.

In our PCT/IL97/00243 published as WO 99/03533 there was disclosed (see also FIGS. 6–8 in that patent application) a device for inhibiting premature labor or stimulating labor contractions. It was stipulated that such device may provide more control over the process of labor than is possible by using drugs.

Several situations were considered:
a. stopping premature labor;
b. stopping a labor where a cesarean section is indicated;
c. situations where fine control of the force of contractions of the uterus is required;
d assisting a labor which is not advancing properly;
e. stopping labor from ever starting, where it is contra-indicated;
f dictating a preferred contraction profile during labor.

It is a main object of the present invention to provide uterus controlling device and method that provides for induction of labor, even where it has not begun.

Another main purpose of the present invention is to provide uterus controlling device and method for inhibition of labor contractions.

Another object of the invention is to provide such device and method that allows for refined control of the uterus, governing the amplitude, timing, duration of the uterus contractions, thus achieving substantial control over labor, either initiating, enhancing or inhibiting labor contractions.

Yet another object of the invention is to provide several modes of operation of such device and method so as to accomplish various goals and objects relating to labor and control of the uterus.

There is thus provided, in accordance with a preferred embodiment of the present invention, a method for controlling uterine contractions in a female comprising:

providing at least one of a plurality of sensors adapted to sense uterine contractions;

providing an electric signal generator;

providing a control unit adapted to receive the signal from said at least one of a plurality of sensors and actuate said signal generator to generate a non-excitatory electric signal in a predetermined timing and duration with respect to a sensed uterine contraction;

providing electric signal delivery means for the delivery of electric signal from the electric signal generator to at least one of a plurality of predetermined locations on the uterus;

sensing a uterine contraction using said at least one of a plurality of sensors; and applying non-excitatory electric field at said at least one of a plurality of predetermined locations on the uterus in predetermined timing and duration with respect to the sensed uterine contraction.

Furthermore, in accordance with another preferred embodiment of the present invention, there is provided a method for enhancing uterine contractions in a female comprising:

providing at least one of a plurality of sensors adapted to sense uterine contractions;

providing an electric signal generator;

providing a control unit adapted to receive the signal from said at least one of a plurality of sensors and actuate said signal generator to generate a non-excitatory electric signal in a predetermined timing and duration with respect to the sensed uterine contraction;

providing electric signal delivery means for the delivery of electric signal from the electric signal generator to at least one of a plurality of predetermined locations on the uterus;

sensing a uterine contraction using said at least one of a plurality of sensors; and applying non-excitatory electric field at said at least one of a plurality of predetermined locations on the uterus in a predetermined timing and duration with respect to the sensed uterine contraction.

Furthermore, in accordance with another preferred embodiment of the present invention, there is provided a method for controlling uterine contractions in a female comprising:

providing at least one of a plurality of sensors adapted to sense uterine contractions;

providing an electric signal generator;

providing a control unit adapted to receive the signal from said at least one of a plurality of sensors and actuate said signal generator to generate a non-excitatory electric signal in a predetermined timing and duration with respect to the sensed uterine contraction;

providing electric signal delivery means for the delivery of electric signal from the electric signal generator to at least one of a plurality of predetermined locations on the uterus;

sensing a uterine contraction using said at least one of a plurality of sensors; and applying non-excitatory electric field at said at least one of a plurality of predetermined locations on the uterus in a predetermined timing and duration with respect to the sensed uterine contraction, said electric field commencing not before the commencement of the uterine contraction.

Furthermore, in accordance with another preferred embodiment of the present invention, the method is used for enhancing uterine contractions, and the non-excitatory electric field is terminated not later than the end of a peaked substantially plateau level in said contraction.

Furthermore, in accordance with another preferred embodiment of the present invention, said at least one of a plurality of sensors is a sensing electrode and wherein the commencement of the contraction is determined by the commencement of erratic electric activity of the uterus sensed by the sensing electrode and the estimated end of a plateau level in said contraction may be determined automatically or manually by the physician by determining the termination of the erratic electric activity.

Furthermore, in accordance with another preferred embodiment of the present invention, said at least one of a plurality of sensors is an intra-uterine pressure sensor and wherein the commencement of the contraction is determined by the commencement of rise in the pressure activity of the uterus sensed by the intrauterine pressure sensor and the end of a plateau level in said contraction is determined by a drop in the intra-uterine pressure level following the peaked substantially plateau level.

Furthermore, in accordance with another preferred embodiment of the present invention, the duration of the applied non-excitatory electric field is not greater than about 10 percent of the duration of the contraction cycle.

Furthermore, in accordance with another preferred embodiment of the present invention, the non-excitatory electric field is applied with a delay after the commencement of the uterine contraction.

Furthermore, in accordance with another preferred embodiment of the present invention, the non-excitatory electric field comprises a substantially constant non-excitatory electric field.

Furthermore, in accordance with another preferred embodiment of the present invention, the substantially constant non-excitatory electric field is stopped before the anticipated commencement of a uterine contraction.

Furthermore, in accordance with another preferred embodiment of the present invention, said electric field has a square waveform.

Furthermore, in accordance with another preferred embodiment of the present invention, said electric field has a trapezoidal waveform.

Furthermore, in accordance with another preferred embodiment of the present invention, said electric field ends in a gradual drop.

Furthermore, in accordance with another preferred embodiment of the present invention, the gradual drop is linear.

Furthermore, in accordance with another preferred embodiment of the present invention, the gradual drop is non-linear.

Furthermore, in accordance with another preferred embodiment of the present invention, said plurality of sensors comprise sensing electrodes for measuring electromyography (EMG) signals.

Furthermore, in accordance with another preferred embodiment of the present invention, in order to synchronize output waves to uterine contractions at least one of said plurality of sensors is placed on the abdomen of the female.

Furthermore, in accordance with another preferred embodiment of the present invention, said plurality of sensors comprise intra-uterine pressure sensors.

Furthermore, in accordance with another preferred embodiment of the present invention, said plurality of sensors comprise mechanical sensors.

Furthermore, in accordance with another preferred embodiment of the present invention, said mechanical sensors comprise strain gauge sensors.

Furthermore, in accordance with another preferred embodiment of the present invention, said strain gauge sensors are placed on the abdomen of the female.

Furthermore, in accordance with another preferred embodiment of the present invention, said at least one of a plurality of sensors is inserted vaginally and placed in contact with the cervix.

Furthermore, in accordance with another preferred embodiment of the present invention, said electric signal delivery means comprise at least one of a plurality of electrodes.

Furthermore, in accordance with another preferred embodiment of the present invention, said electrodes are selected from stitch electrodes, patch electrodes, net-like electrodes.

Furthermore, in accordance with another preferred embodiment of the present invention, said electrodes are deployed transcutanouesly.

Furthermore, in accordance with another preferred embodiment of the present invention, said electrodes are deployed vaginally.

Furthermore, in accordance with another preferred embodiment of the present invention, said at least one of a plurality of electrodes is placed in the fundus vicinity.

Furthermore, in accordance with another preferred embodiment of the present invention, said control unit continuously samples said at least one of a plurality of sensors input and estimates the timing of initiation of said sensed contractions, the magnitude of said sensed contractions, and the rhythm of said contractions, whereby the magnitude of the contractions, and the rhythm of sensed contractions are used to estimate the progression of the labor process in time to determine a necessity for any electrical intervention or determine the need to terminate the therapy.

Furthermore, in accordance with another preferred embodiment of the present invention, said non-excitatory electric field is applied in synchrony with the sensed uterine contractions.

Furthermore, in accordance with another preferred embodiment of the present invention, said control unit is programmable.

Furthermore, in accordance with another preferred embodiment of the present invention, the non-excitatory electric field is applied in duration in the range of 100 milliseconds to 5 seconds.

Furthermore, in accordance with another preferred embodiment of the present invention, the non-excitatory electric field strength is in the range of 500 microamperes to 20 milliamperes.

Furthermore, in accordance with another preferred embodiment of the present invention, the non-excitatory electric field strength is in the range of 2 to 6 milliamperes.

Furthermore, in accordance with another preferred embodiment of the present invention, the method is used for slowing the rhythm of contractions but substantially retaining the amplitude of contractions, wherein the non-excitatory electric field duration is in the range of 6 to 10 seconds.

Furthermore, in accordance with another preferred embodiment of the present invention, the method is used for inhibiting uterine contractions, wherein the non-excitatory electric field is in the range of 10 seconds to 100 seconds.

Furthermore, in accordance with another preferred embodiment of the present invention, the method is applied in conjunction with drug therapy.

Furthermore, in accordance with another preferred embodiment of the present invention, there is provided a device for controlling uterine contractions comprising:

at least one of a plurality of sensors adapted to sense uterine contractions;

an electric signal generator; and a control unit adapted to receive signals from said sensors and actuate said signal generator in a predetermined manner.

Furthermore, in accordance with another preferred embodiment of the present invention, said electric signal generator is adapted to generate a substantially constant non-excitatory electric field.

Furthermore, in accordance with another preferred embodiment of the present invention, said electric signal generator is adapted to occasionally switch the polarity of said non-excitatory electric field so as to reduce ionic polarization effects.

Furthermore, in accordance with another preferred embodiment of the present invention, said electric signal generator is adapted to stop said substantially constant non-excitatory electric field before the anticipated commencement of a uterine contraction.

Furthermore, in accordance with another preferred embodiment of the present invention, said electric signal generator is adapted to apply the non-excitatory electric field in synchrony with the sensed uterine contractions.

Furthermore, in accordance with another preferred embodiment of the present invention, the electric signal generator is adapted to apply said non-excitatory electric field with a time delay with respect to the commencement of a uterine contraction.

Furthermore, in accordance with another preferred embodiment of the present invention, said plurality of sensors comprise sensing electrodes for measuring EMG signals.

Furthermore, in accordance with another preferred embodiment of the present invention, at least one of said plurality of sensors is adapted to be placed on the abdomen of the female in order to synchronize output waves to spontaneous uterine contractions.

Furthermore, in accordance with another preferred embodiment of the present invention, said plurality of sensors comprise intrauterine pressure sensors.

Furthermore, in accordance with another preferred embodiment of the present invention, said plurality of sensors comprise mechanical sensors.

Furthermore, in accordance with another preferred embodiment of the present invention, said mechanical sensors comprise strain gauge sensors.

Furthermore, in accordance with another preferred embodiment of the present invention, said strain gauge sensors are adapted to be placed on the abdomen of the female.

Furthermore, in accordance with another preferred embodiment of the present invention, said at least one of a plurality of sensors is adapted to be inserted vaginally and placed in contact with the cervix.

Furthermore, in accordance with another preferred embodiment of the present invention, said electric signal delivery means comprise at least one of a plurality of electrodes.

Furthermore, in accordance with another preferred embodiment of the present invention, said electrodes are selected from stitch electrodes, patch electrodes, net-like electrodes.

Furthermore, in accordance with another preferred embodiment of the present invention, said electrodes are adapted to be deployed transcutanouesly.

Furthermore, in accordance with another preferred embodiment of the present invention, said electrodes are adapted to be deployed vaginally.

Furthermore, in accordance with another preferred embodiment of the present invention, said at least one of a plurality of electrodes is adapted to be placed in the fundus vicinity.

Furthermore, in accordance with another preferred embodiment of the present invention, said control unit is adapted to continuously sample said at least one of a plurality of sensors input and estimate the timing of initiation of said sensed contractions, the magnitude of said sensed contractions, and the rhythm of said contractions, whereby the magnitude of the contractions, and the rhythm of contractions are used to estimate the progression of the labor process in time to determine a necessity for any electrical intervention or determine the need to stop the therapy.

Furthermore, in accordance with another preferred embodiment of the present invention, said control unit is programmable.

Furthermore, in accordance with another preferred embodiment of the present invention, said electric signal generator is adapted to generate electric field having a square waveform.

Furthermore, in accordance with another preferred embodiment of the present invention, said electric signal generator is adapted to generate electric field having a trapezoidal waveform.

Furthermore, in accordance with another preferred embodiment of the present invention, said electric signal generator is adapted to generate electric field that ends in a gradual drop.

Furthermore, in accordance with another preferred embodiment of the present invention, the electric signal generator is adapted to generate a non-excitatory electric field having a duration in the range of 100 milliseconds to 5 seconds.

Furthermore, in accordance with another preferred embodiment of the present invention, the electric signal generator is adapted to generate a non-excitatory electric field of a strength in the range of 500 microamperes to 20 milliamperes.

Furthermore, in accordance with another preferred embodiment of the present invention, the electric signal generator is adapted to generate a non-excitatory electric field of a strength in the of 2 to 6 milliamperes.

Furthermore, in accordance with another preferred embodiment of the present invention, the device is designed for slowing the rhythm of contractions but substantially retaining the amplitude of contractions, wherein the electric signal generator is adapted to generate a non-excitatory electric field with duration in the range of 6 to 10 seconds.

Finally, in accordance with another preferred embodiment of the present invention, the device is designed for inhibiting uterine contractions, wherein the electric signal generator is adapted to generate a non-excitatory electric field in the range of 10 seconds to 100 seconds.

BRIEF DESCRIPTION OF THE FIGURES

In order to better understand the present invention, and appreciate its practical applications, the following Figures are provided and referenced hereafter. It should be noted that the Figures are given as examples only and in no way limit the scope of the invention as defined in the appending claims. Like components are denoted by like reference numerals.

FIG. 3 shows another set of charted test results of inhibitory uterus contractility modulation sequence applied on a rat, the contractions sensed with strain gauge sensors.

FIG. 4a illustrates charted test results of enhancing UCM (Uterus Contractility Modulation) signals, enhancing labor contractions in a pre-partum rat.

FIG. 4b illustrates charted test results of applying enhancing UCM signals in conjunction with administration of a labor-inducing drug (oxytocin), enhancing labor contractions in a pre-partum rat.

FIG. 6 illustrates intra uterine pressure charted test results of applying enhancing UCM signals on spontaneous uterine contractions of a pre-partum rabbit.

DESCRIPTION OF THE INVENTION AND FIGURES

Figure 1:
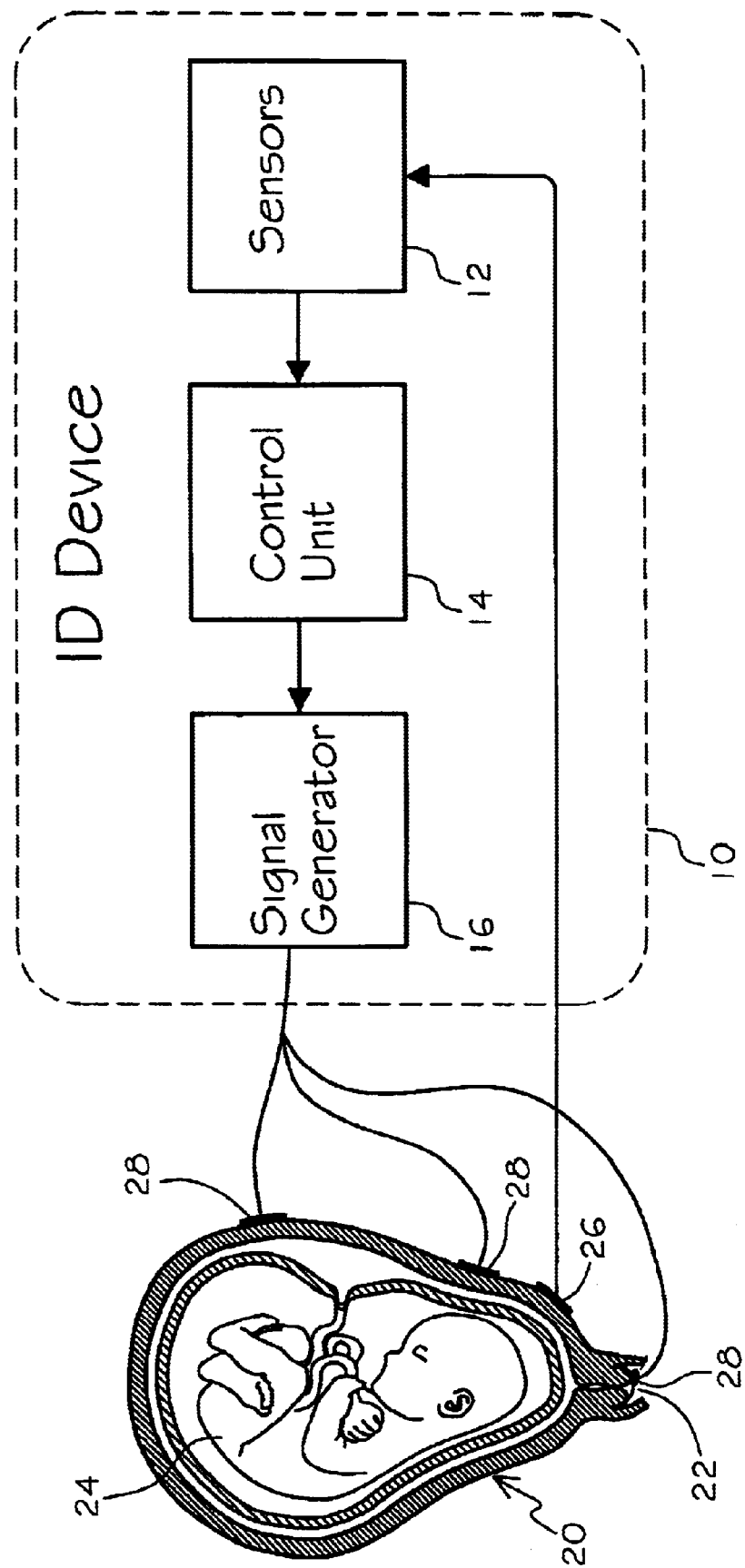
FIG. 1 is a schematic general presentation of a uterus contractility modulation device according to a preferred embodiment of the present invention.

Labor is a normal process that occurs for most pregnant women after the 37th week of pregnancy. When the uterus is "ripe" for labor, uterine contractions, that are present almost throughout the entire pregnancy period but are irregular, unnoticed or just noticed (Braxton-Hicks), suddenly become noticeably longer, more intense and painful. After some time that may vary from female to female, an orderly periodic contraction regime is established and the strength (or amplitude) of the contractions rise to what is called "pressure contractions", which are effective labor contractions, and their duration becomes substantially constant, signaling the commence of labor. At the start of the labor process uterine contractions arrive every 4–5 minutes and last some 45 to 60 seconds. Each uterine contraction is usually characterized by three consecutive stages. At first the intra-uterine pressure, initially at a baseline level, rises (hereafter—intra-uterine pressure rise), then it reaches a peak characterized by a substantial plateau in the level of pressure (hereafter—intra-uterine pressure level plateau) and finally the intra-uterine pressure drops (hereafter—intra-uterine pressure drop) to the initial baseline. The uterine electric activity corresponding to a uterine contraction is characterized by the occurrence of substantially erratic electric activity, associated with opening of voltage-gate calcium channels in the uterine muscle cells. This erratic electric activity appears as spikes in the electric chart. It was found that the erratic electric activity associated with a uterine contraction slightly precedes the intra-uterine pressure activity associated with that contraction.

The causes of Preterm labor are not well known, but it is estimated that about 6–8 percent of pregnant women will develop labor between the 20th and the 37th week of their pregnancy resulting in a premature birth.

An overdue pregnancy, on the other hand is pregnancy lasting more than 40 weeks. In overdue pregnancies the risk to the fetus is that it over-develops and becomes too big to pass through the mother's birth canal making cesarean operation necessary. If pregnancy completes 42 weeks doctors usually recommend an induced labor to be carried out.

The inventors of the present invention have found that the applying of non-excitatory electrical signal on the uterus in a predetermined manner may either induce or inhibit labor contractions, as it is disclosed herein.

A main aspect of the present invention is the induction of labor by electrical non-excitatory stimulation of uterus contractions.

Another main aspect of the present invention is the inhibition of labor by electrical relaxation of the uterus, causing inhibition of labor contractions.

Another aspect of the present invention is the provision of acute treatment with external device during hospitalization, or the enablement of short-term implantation of an implantable device.

Another main aspect of the present invention is the use of non-excitatory electrical signals, thus achieving localized control without initiating propagating action potentials across the uterus.

The present invention is hereafter explained with reference to the accompanying drawings. The drawings are provided for better understanding of the invention and in no way limit the scope of the invention as defined by the appended claims.

Uterine contractions can be sensed and measured in various ways. For example strain gauge sensors may be placed on the pregnant female's abdomen to sense changes in the circumference of the abdomen indicating uterine contractions. Pressure sensor may be placed Intra-uterinally to measure pressure changes, the increase in pressure indicating the occurrence of contraction.

It is known that the electric conduction characteristics of the uterus change within 24 hours prior to the commencing of labor, when the uterus is "ripe" to begin labor. Gap junctions facilitating electric conduction between cells appear and grow in numbers so as to allow conductance between adjoining cells. Electrical activity of the uterus corresponds to uterine contractions and may be monitored by sensing electrical activity via electrodes placed on locations on the uterus (for example attaching an electrode to the cervix vaginally, or attaching electrodes to the uterus wall transcutaneously) or placing electrodes on the abdomen in close proximity to the uterus. It was found and is noted that for each contraction the commencing of electrical activity associated with uterine contraction antecedes the actual commencing of mechanical contraction.

FIG. 1 is a schematic general presentation of a uterus controller according to a preferred embodiment of the present invention.

The device 10 generally comprises sensing means, control unit and signal generator.

The sensing means comprise at least one of a plurality of sensors 26 that are adapted to be located on the uterus walls 20, or in its vicinity (even placed on the abdomen). Penetration of the uterus walls is believed to be undesired as it may cause irreversible damage to the uterus or harm the fetus 24. In a preferred embodiment of the present invention the sensors comprise electrodes. In order to synchronize the output waves to spontaneous contractions one or more electrodes will be placed on the abdomen. EMG signals measured from these electrodes are used as indications for uterine activity. An optional intrauterine pressure (IUP) input is available in cases when the physician inserts such a catheter to the uterus. In that case the uterus contractility modulation device is able to synchronize the UCM (Uterus Contractility Modulation) signal of the present invention according to the timing of the mechanical activity or the electrical activity corresponding to the mechanical activity of the uterus.

The sensors may also be mechanical sensors, such as strain gauge sensors, and may be located on the abdomen of the patient (attached by contact to the skin, a belt, in the form of a sticker or any other attachment) Other sensor type may be sensors attached to the cervix from the outside (vaginally). Yet another type of sensors that may be used is a pressure sensor such as intrauterine pressure catheter (for example such as the ones manufactured by Millar).

The signal generator 16 is adapted to generate a set of pre-defined waveform and outputs according to commands received from the control unit. The electrodes 28 that deliver the electric field generated by the signal generator 16 to the uterus 20 may be of various types, such as stitch electrodes, or patch electrodes They may be transcutaneous or attached to the abdomen. Net-like electrode may be used to access and thus control wider areas of the uterus (like the one disclosed in PCT/IL97/00243).

In another preferred embodiment the electrodes may be inserted vaginally and attached to the cervix 22.

It is believed that in some cases the effectiveness of the treatment may be enhanced if electrodes are placed in the fundus vicinity. That may be the case when the fundus is where the contractions originate. There are also other cases where the main pacemaker of the myometrium is located in other areas of the uterus, in which case the most effective location for UCM signal application may be different.

A control unit 14, for the interpretation of data received from the sensors and decision making and control of the signal generation unit, is adapted to identify events sensed by the sensors 26 and control the signal generator initiating signals in a predetermined manner The control unit is preferably adapted to be accessed by a user via user interface, so as to allow user's determining the appropriate mode of operation, but the control unit may also include a CPU that includes a predefined algorithm so as to provide electric signals in a predetermined manner. Since in a preferred embodiment of the invention the device may be implantable, it s suggested to allow programming of the device control by electromagnetic induction, as in pacemakers. In a preferred embodiment of the uterus contractility modulation device of the present invention the control unit receives as input the EMG signals from the abdomen electrodes and makes a real time estimation of spontaneous uterine contractions. According to the mode of operation programmed by the physician it initiates commands for the signal generator unit regarding the waveform shape and timing.

The control unit continuously samples the sensor's input and estimates the following basic parameters: timing of initiation of each contraction, current magnitude of contractions, and current rhythm of contractions. The current magnitude of contractions, and current rhythm of contractions are used to estimate the progression of the labor process in time and detect a necessity for any electrical intervention or the possibility to stop the therapy.

In one preferred embodiment of the uterus contractility modulation device of the present invention, the device is operated by a physician who attaches the electrodes and programs the device using proprietary software running on a PC. After a time of 20–60 minuets contractions should decrease significantly to a level, which is related to a non-labor state, or increase to a level of labor contractions, depending on the desired application. The physician should then turn off signal using the control PC and continue to monitor electrical sensing and mechanical contraction.

In a preferred embodiment of the present invention a uterus contractility modulation device is used to reduce mechanical activity of the uterus by applying a synchronized electrical signal to the uterus. The device is operated by a physician in an ambulatory environment and indicated for use in medical situations where it is desired to inhibit uterus contraction activity, such as reduction of uterus contractions in order to delay preterm delivery, reduction of uterus contractions during intra-uterine fetal surgery, reduction of uterus contractions of pregnant women undergoing a non obstetrical abdominal operation (appendicitis, cholecystitis etc), or other such situations.

In another embodiment of the present invention a uterus contractility modulation device is used to enhance mechanical activity of the uterus.

In another embodiment of the present invention the control unit is programmed to automatically determine from the sensed uterine activity the existence of a uterine contraction, its duration, amplitude and regime and output the desired signal through electric signal delivery means (electrode leads for example) to the uterus—be it enhancing or inhibiting signal, as is later explained.

It is assumed that for standard operation at least two or three electrodes must be used. One electrode (a single elastic electrode) is to be attached to the cervix using a speculum. The electrode is non-invasive and does not penetrate the cervix. One side of the electrode is connected to the cervix with an elastic mechanism and the other side is electrically connected through a wire going out of the vagina to the device. This electrode is generally multi-polar though only a single pole is needed. This allows the physician to select the best electrode, which gives the best geometrical configuration. A second electrode has preferably the shape of a patch with a size of about 25 mm×25 mm and is located on the abdomen. This is a unipolar electrode. A third electrode—used for sensing electrical activity—must be attached to the abdomen. The electrode is bipolar and is used to collect data on the spontaneous activity of the uterus.

After attaching the electrodes the physician views the sensing signal on the control PC for a certain period of time to determine the condition of the contractions and selects the trigger parameters—the critical parameters that will actuate the various activity modes of the device—accordingly. He then activates the signal and watches the changes in the mechanical contractions and the electrical sensing.

In accordance with a preferred embodiment of the invention, local control of the force of contraction and/or the sensitivity of portions of the uterus to excitation is achieved by applying local, non-excitatory electric fields.

In accordance with a preferred embodiment of the invention, local control of the force of contraction and/or the sensitivity of portions of the uterus to excitation is achieved by applying local, non-excitatory electric fields directly to the portion to be controlled. Although such non-excitatory electric fields do not create a propagating action potential in the controlled portion the electric field does modify the response of the portion to an artificial or naturally occurring activation signal, when it arrives. In particular, the inventors have found that it is possible to increase or to decrease the force of contraction of a portion of a uterus. In addition, it is possible to desensitize a muscle segment so that it has a reduced reaction or so it does not react at all to normal amplitudes of activation signals. This desensitization, while reversible, may be made to last a certain period of time after the removal of the controlling electric field.

Furthermore, it was found that such non-excitatory electric fields might initiate labor contractions, thus inducing labor.

The term "electric field" has been used to describe the non-excitatory field used to control the uterine muscle. The terms "field" and "current pulse" are used interchangeably herein, since, in the body, both are generated when a voltage potential is created between two electrodes. In a preferred embodiment of the invention, the field is applied by maintaining a constant current between at least two electrodes. Alternatively, a voltage potential may be controlled instead of controlling the current.

The UCM signal of the present invention is a non-excitatory electrical signal that is applied on the uterus in predetermined timing, duration, waveform and amplitude. For the enhancement of uterine contractions the UCM sequence is applied so that each single UCM signal corresponds to a single uterine contraction. In inhibitory UCM treatment a UCM signal corresponds to a uterine contraction but may be applied over time period during which more that one uterine contraction occur. In order for the UCM treatment to be effective a sequence of subsequent UGM signals (hereafter—UCM sequence) need to be applied so as to achieve substantial results.

The main differences between an inhibiting UCM sequence and an enhancing UCM sequence are in the timing of the UCM signal and in the duration of the UCM signal. Generally, enhancing UCM signals are shorter than inhibiting UCM signals. The inventors of the present invention have learned that an enhancing UCM signal should commence not before the commencement of the electric activity associated with a uterine contraction, and may also be applied with a delay after the commencement of such activity. However, the enhancing UCM signal should end before or, at the latest, coincide with the termination of the erratic electric activity, marking the end of the plateau of the intra-uterine pressure level and indicating the start in the intrauterine pressure drop. Failure to terminate the UCM signal on time may induce an activation signal (pacing signal) that may yield an undesired, untimely contraction. As a finger rule it is asserted that an enhancing UCM signal should not be longer than about 10 percent of the duration of a single uterine contraction cycle. Furthermore it is suggested that an enhancing UCM signal be not longer than the duration of the intra-uterine pressure level plateau. The UCM signal may be synchronized with the intra-uterine pressure sensed signal (obtained from intra-uterine pressure sensors) or synchronized with the electrical activity signal (received by electrodes). In the tests conducted by the inventors on rabbits and rats the UCM signals were synchronized with the uterine electric activity, the UCM signal usually applied with zero delay after the commencement of the erratic electric activity associated with a contraction. Nevertheless, the inventors assert that a delay other than zero and/or synchronization with the intra-uterine pressure signal is also in order.

Two particular waveforms of non-excitatory electric fields have been found to be beneficial.

A first type of UCM non-excitatory signal is a substantially constant electric field (whose polarity may be occasionally switched to reduce ionic polarization effects). This field may be applied without any synchronization to the controlled uterine muscle. Such UGM constant electric field is suitable for inhibiting uterine contractions However, the inventors have found it beneficial to stop the inhibiting field shortly before the activation signal is expected to arrive at the controlled uterus (i.e. the commencement of a contraction), so as to reduce the amplitude of activation signal required to excite the controlled uterus. This is recommended due to the possible desensitization of the uterus as a result of the long UCM signal, so that some recovery period between the termination of the UCM signal and the commencing of the contraction is advised.

A second type of UCM non-excitatory signal is a pulse that is applied in synchrony with the arrival of an activation signal. The pulse is applied either before, during the arrival of the activation signal or at a delay after its arrival (a long enough delay after activation is equivalent to applying the pulse before activation—it being the consecutive activation). The inventors assert that a non-excitatory electric field applied after the activation signal tends to increase the force of contraction of the controlled uterus, by increasing plateau duration of the uterine contraction intra-uterine pressure level. It is asserted that a non-excitatory field applied at a greater delay after the arrival of the activation signal extends the relaxation period (possibly by hyperpolarizing the muscle cells so that the activation signal does not cause a depolarization due to desensitization). As a result, at least some of the muscle cells do not respond to the activation signal and the force of contraction of the muscle is reduced. Thus, the stronger the non-excitatory signal, the more cells will be hyperpolarized and the lower will be the force of contraction. In an extreme case, none of the muscle cells will respond to the activation signal and the propagation thereof will be inhibited. It is also possible that the non-excitatory field directly reduces affects the force of contraction achieved by a single muscle fiber.

It is the timing of initiation of each contraction that is used to synchronize the output signal to the correct phase of contraction of the UCM signal.

Typically the inputs for the uterus contractility modulation device of the present invention include information at the bandwidth of between 1 Hz to 40 Hz with voltage range of 0–3 mV (for sensed timing of initiation of each contraction and magnitude of contractions), and at bandwidth of 0–1 Hz (for sensed rhythm of contractions).

Each input is preferably sampled at rate of 150 samples/ sec or higher with at least 8-bit resolution.

Accordingly, the output signal from the uterus contractility modulation device of the present invention may optionally be capable of delivering square waves with typical values of variable widths: 0–60 sec, resolution of 250 ms, tolerance of signal width is ±1% or 10 ms (whichever is higher), current output 0–10 mA with a resolution of 0.5 mA, required current precision is ±0.1 mA. Impedance of electrode can range between 200–1500 Ohms. Other wave shapes may also be suitable, for example trapezoidal wave (see FIG. 8b).

Communication input/output interface (such as RS232) is optionally provided to the control unit to program all system parameters and transmit real time sense signals sampled from the input. Maximal delay in transmitting a sensed signal is preferably 1 sec. The UCM signal is applied according to the signal on/off parameter programmable through the RS232 communication interface and an external switch. In any given time there is a single input defined as the detection input The detection input is used to synchronize the UCM signal that is applied according to the signal on/off parameter. Programmable parameters may include: detection input, UCM signal width, UCM signal amplitude, UCM signal delay, UCM signal baseline level, sensed trigger level, signal window length, UCM on/of.

Initial tests for the uterus contractility modulation device and method of the present invention were carried out on pregnant rats and rabbits, the results presented in FIGS. 2–6.

It was found for rats and rabbits that enhancing UCM signals may preferably be in the range of 100 milliseconds to 5 seconds in duration (of a single signal), and in range of 500 microamperes to 20 milliamperes in strength (of a single signal). It was found that best results appeared when the signal strength was in the range of 2 to 6 milliamperes. Furthermore it was found that signals with duration of 6 to 10 seconds resulted in decrease in rhythm but little decrease in amplitude of contractions, whereas enhancing UCM signals in the range of 10 seconds to 100 seconds resulted in substantial decrease in contraction amplitude as well as in decrease of contraction rhythm. It is anticipated that for human pregnant females the above referenced parameters should be substantially the same. It is noted, however, that the UCM device and method of the present invention has not been tested yet on humans, and that such tests may find that the typical parameter values for uterus contractility modulation in humans may slightly or substantially differ from these referenced above.

Figure 2:
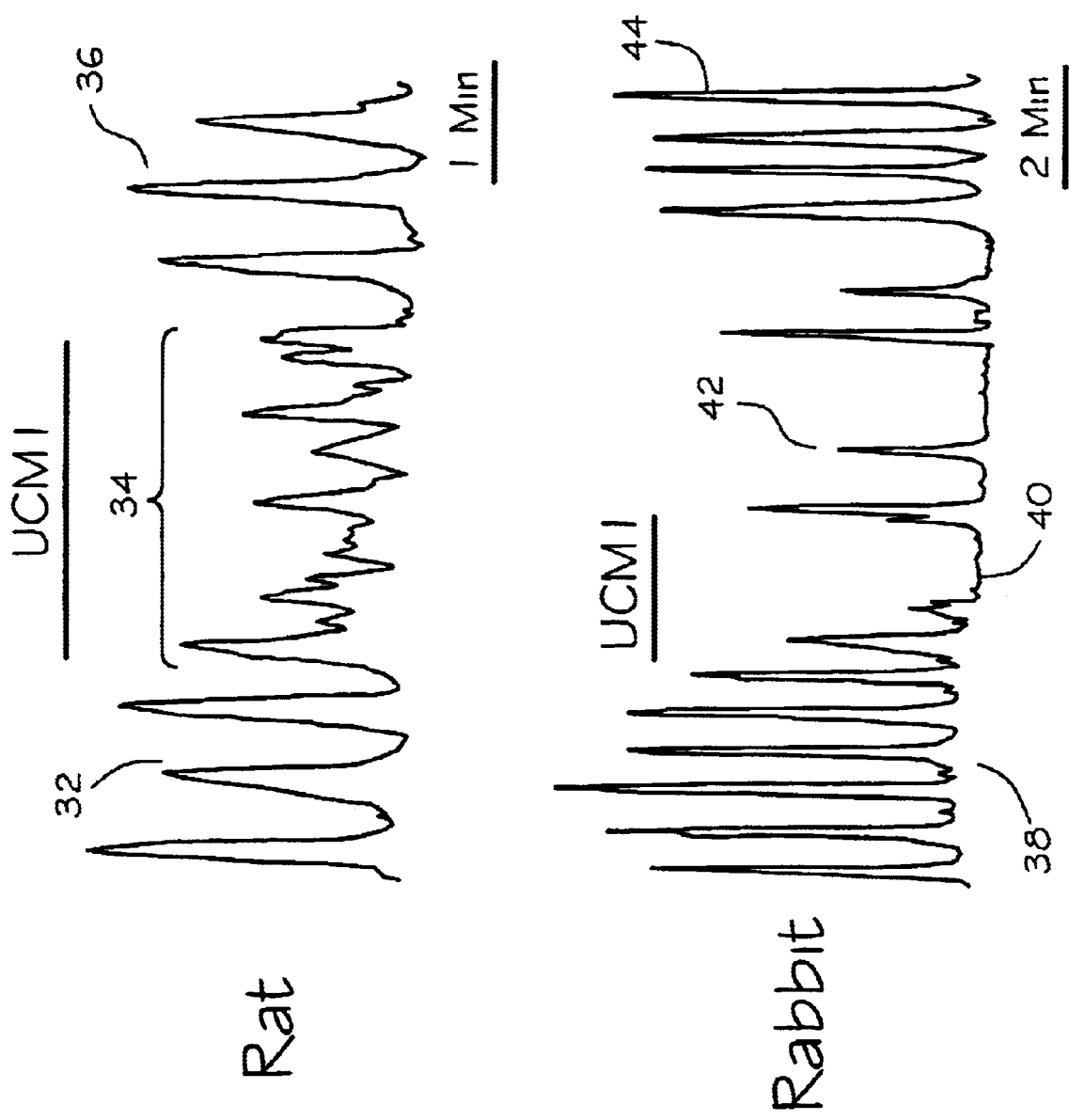
FIG. 2 illustrates charted test results of applying inhibitory uterus contractility modulation sequence on pregnant rat and rabbit experiencing spontaneous uterine contractions.

FIG. 2 illustrates charted test results of applying inhibitory uterus contractility modulation sequence on pregnant rat and rabbit experiencing spontaneous uterine contractions.

Shown are charted recorded contractions (sensed by a strain gauge) over time. At first uterine contractions are present (32 in the rat, 38 in the rabbit). Then inhibitory uterine contractility modulation sequence (UCM1) is applied and the contractions are substantially weakened (34 in the rat, 40 in the rabbit). The rabbit even stops experiencing contractions for a while 42. After a while (when the uterine contractility modulation signals are not further applied labor contractions reappear (36, 44). Note that the bar marked UCM represents the total duration of the UCM sequence. As mentioned earlier a UCM sequence comprises a series of UCM signals, each corresponding to a single uterine contraction.

FIG. 3 shows another set of charted test results of inhibitory uterus contractility modulation sequence applied on a rat, the contractions sensed with strain gauge sensors. At first strong labor contractions are experienced (50), then when UCM inhibitory sequence is applied the contractions decrease in magnitude. After the UCM sequence is stopped the original magnitude of contractions reappears 54.

FIG. 4a illustrates charted test results of enhancing UCM (Uterus Contractility Modulation) signals, enhancing labor contractions in a pre-partum rat. At first uterine contractions are weak 60. When applying UCM enhancing signals, uterine contractions gain strength and become steady 62. After UCM signals are stopped the contractions weaken and appear disordered 64.

FIG. 4b illustrates charted test results of applying enhancing UCM signals in conjunction with administration of a labor-inducing drug (oxytocin), enhancing labor contractions in a pre-partum rat. At first contractions are sporadic 70. Oxytocin is introduced and as a result the amplitude, as well as the rhythm, of contractions increase 72. Still under the influence of oxytocin UCM enhancing signals are provided and as a result the contractions become steady and uniform 74. After UCM signals are stopped disordered contractions appear 76.

Figure 5A:
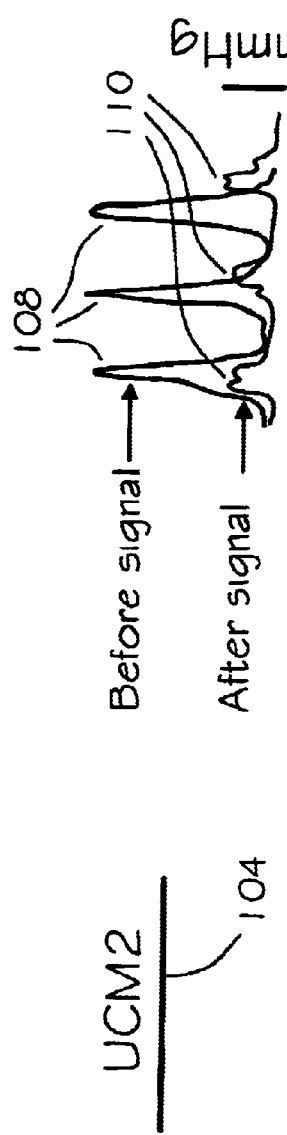
FIG. 5a illustrates intra uterine pressure charted test results of applying inhibitory UCM signals on premature labor contractions of a pre-partum rabbit.

FIG. 5a illustrates intra uterine pressure charted test results of applying inhibitory UCM signals on premature labor contractions of a pre-partum rabbit.

Initially the pre-partum rabbit experiences premature labor contractions 102 that are very strong (about 20 mm Hg). UCM sequence 104 in accordance with the present invention is applied causing immediate and substantial reduction in the level of contractions about a quarter in amplitude from the initial strength, and after the UCM sequence is stopped 106 the uterine contractions remain contained at the same level for a long period of time (in the actual test the contained inhibited contractions lasted for about two hours after the conclusion of the UCM sequence before the rabbit was disconnected from the test apparatus).

Figure 5B:
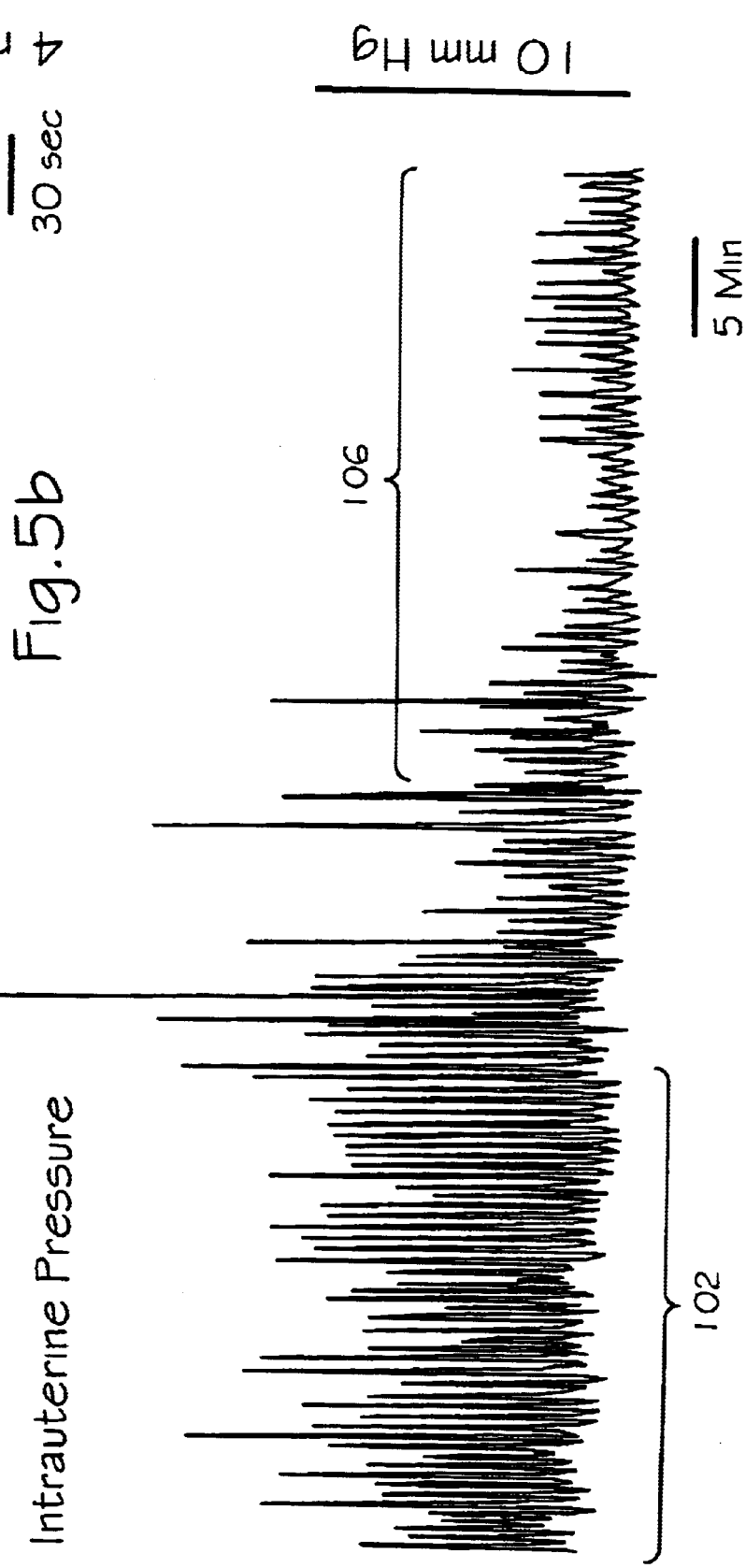
FIG. 5b depicts and highlights details from the chart of FIG. 5a, comparing three superposed uterine contractions before and after the UCM sequence was applied.

FIG. 5b depicts and highlights details from the chart of FIG. 5a, comparing three superposed uterine contractions before and after the UCM sequence was applied. It is evident that while the initial contractions 108 are stronger (higher in the chart) and more frequent (closer in the chart) the inhibited contractions after the UCM treatment are milder (lower in the chart) and with greater pauses in between (further apart in the chart).

FIG. 6 illustrates intra uterine pressure charted test results of applying enhancing UCM signals on spontaneous uterine contractions of a pre-partum rabbit.

At first uterine contractions 112 are mild. Then UCM sequence 114 is applied and the amplitude and frequency of contractions 116 increases noticeably.

Figure 7A:
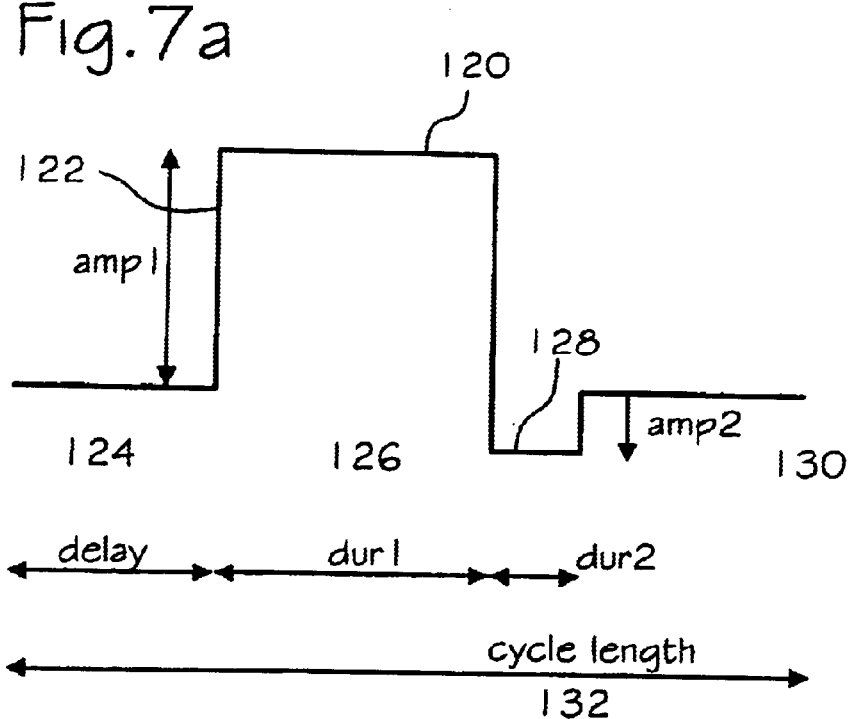
FIGS. 7a and 7b illustrate two optional waveforms for the UCM signal.

FIG. 7a illustrates a square UCM signal waveform 120 suitable for UGM treatment. The following parameters are given only as an example and by no means limit the scope of the present invention. Delay 124 is the time from detection of spontaneous/paced contraction to signal delivery (0–1000 ms). dur1 126 is a period of time in which constant current is delivered beginning after delay (2–30 sec). amp1 122 is the amplitude of current during dur1 126 (0–1 mA for uterus wall, 5–15 mA for abdominal/cervical electrodes). dur2 128 is the period of time in which constant current is applied negative in polarity and different in amplitude from amp1 (50–300 ms) in order to reduce ionic polarization effects. Amp2 130 is the amplitude of current during dur2 128 (0–1 mA). cycle length 132 is the minimal time between two signal deliveries (20–80 sec for humans), corresponding to the cycle of uterine contractions.

Figure 7B:
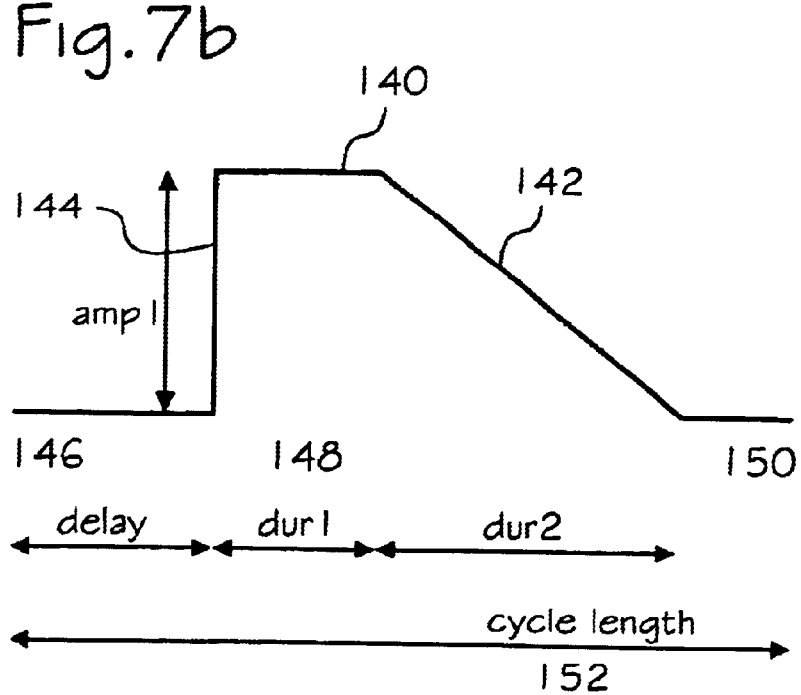

FIG. 7b illustrates a trapezoidal waveform 140 suitable for UCM treatment. The following parameters are given only as an example and by no means limit the scope of the present invention. Delay 146 is the time from detection of spontaneous/paced contraction to signal delivery (0–1000 ms), dur1 148 is the period of time in which constant current is delivered beginning after delay 146 (2–30 sec), amp1 144 is the amplitude of current during dur1 148 (0–1 mA for uterus wall, 5–15 mA for abdominal/cervical electrodes), dur2 150 is the period of time in which the current fades linearly from amp1 to zero (2–20 sec) demonstrating a slope 142, cycle length 152 is the minimal time between two signal deliveries (20–80 sec for humans) corresponding to the cycle of uterine contractions. The drop in the current (dur2), which is gradual, does not have to be linear, and may also be non-linear (for example: exponential, hyperbolic or in any other diminishing form).

Figure 8A:
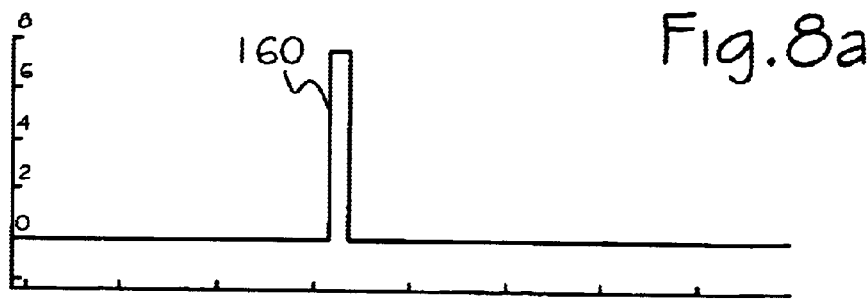
FIGS. 8a, 8b and 8c illustrate the relation between the electrical activity of a rabbit uterus, the intra uterine pressure during a uterine contraction and the timing of an enhancing UCM square signal with respect to that contraction.
Figure 8B:
Figure 8C:
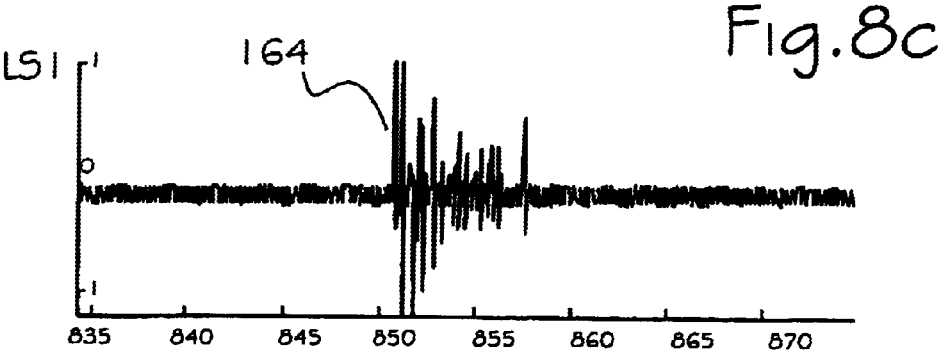

FIGS. 8a, 8b and 8c illustrate the relation between the electrical activity of a rabbit uterus, the intra uterine pressure during a uterine contraction and the timing of an enhancing UCM square signal with respect to that contraction. All figures correlate sharing the same time scale (the X axis), FIG. 8b showing a plot of a rabbits intra-uterine pressure readings against time, FIG. 8c showing a plot of the electrical activity of the uterus with respect to time and FIG. 8a showing the UCM signal applied on the rabbit's uterus with respect to time. It is evident that the rise in intra-uterine pressure 162 associated with a uterine contraction correlates to rise in the uterine electrical activity 164. An enhancing square UCM signal 160 is given with a zero delay after the commencing of the erratic electric activity.

Note that the electrical activity shown in FIG. 8c appears to be commencing after the commencement of the pressure wave in FIG. 8b. An electrical sense measured in the uterus is local and can therefore appear anywhere during the rising edge of pressure wave which is global. For many women the propagation pattern of electrical activity and the location of uterine pacemaker are known and therefore an early detection can be achieved by locating the sensing electrode in the vicinity of the pacemaker. Nevertheless, late timing due to unknown pacemaker location or propagation pattern will have a small (if any) impact on the contractility modulation effect since the propagation speed is high enough to keep the total propagation time over the whole uterus small and limited to the rising edge of the pressure pulse.

Figure 9A:
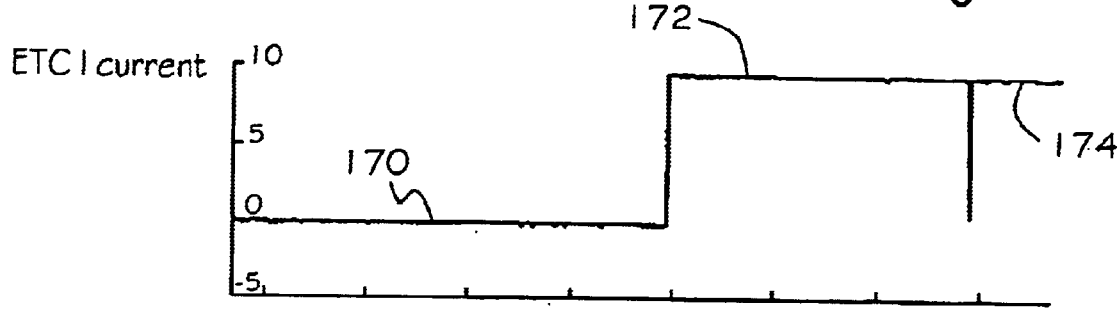
FIGS. 9a, 9b and 9c illustrate the relation between the electrical activity of a rabbit uterus, the intra uterine pressure and the timing of an inhibitory UCM square signal with respect to a uterine contraction.
Figure 9B:
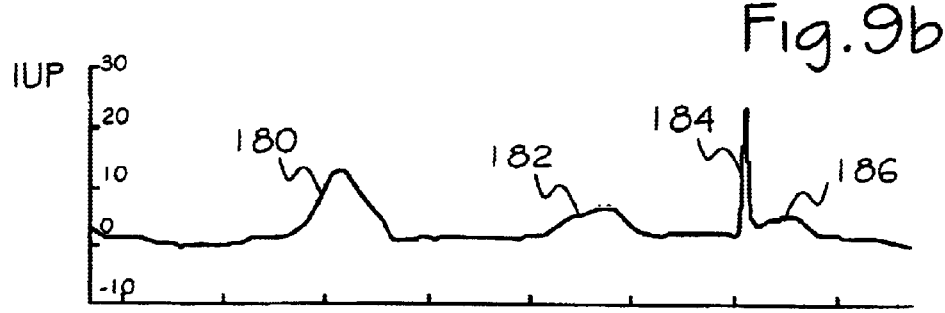
Figure 9C:
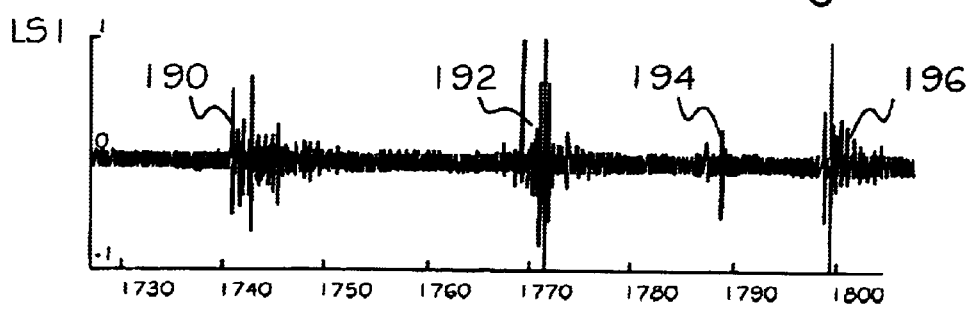

FIGS. 9a, 9b and 9c illustrate the relation between the electrical activity of a rabbit uterus, the intra uterine pressure and the timing of an inhibitory UCM square signal with respect to a uterine contraction. All figures correlate sharing the same time scale (the X axis). Again, FIG. 9b shows a plot of a rabbit's intra-uterine pressure readings against time, FIG. 9c shows a plot of the electrical activity of the uterus with respect to time and FIG. 9a shows the UCM signal applied on the rabbit's uterus with respect to time. At first there is a period 170 with no application of a UCM signal. A spontaneous uterine contraction shows both in corresponding rises in the intrauterine pressure 180 and in the electrical activity 190. An inhibitory square UCM signal 172 is applied just as a consecutive contraction (182, 192) commences. As a result this contraction is noticeably milder than the previous one. The UCM signal 172 is immediately followed by a consecutive square UCM signal 174, juxtaposed to the previous one. A second inhibited contraction (186, 196) follows—preceded by a small irregular contraction expressed as a spike 184 in the intra-uterine pressure plot and a corresponding erratic short electric activity 194.

Figure 10A:
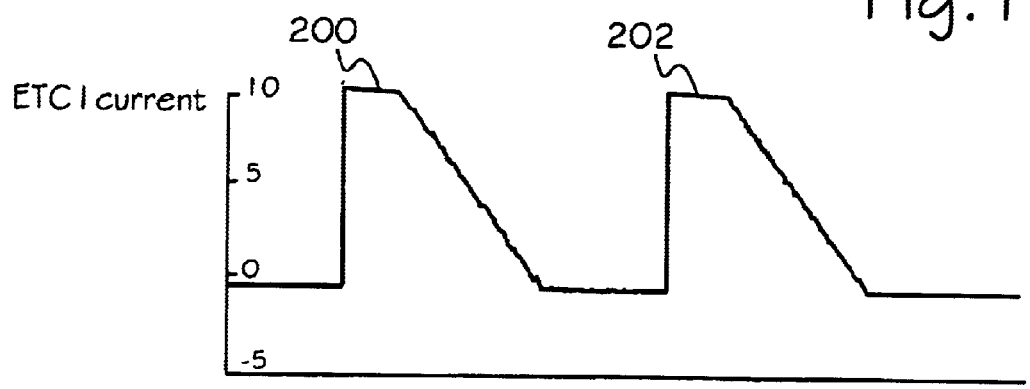
FIGS. 10a, 10b and 10c illustrate the relation between the electrical activity of a rabbit uterus, the intra uterine pressure and the timing of an inhibitory UCM trapezoidal signal with respect to a uterine contraction.
Figure 10B:
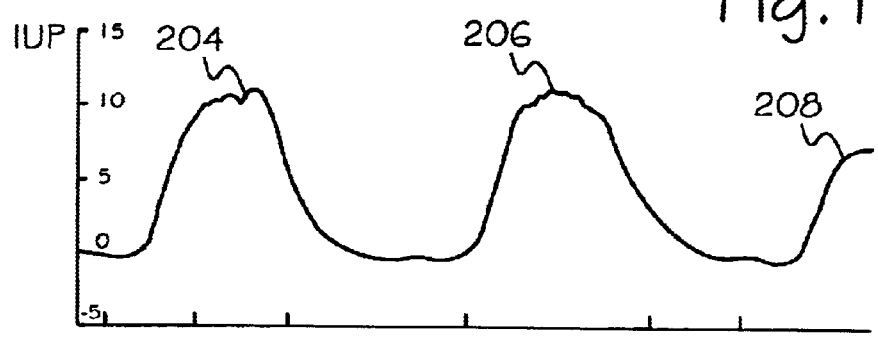
Figure 10C:
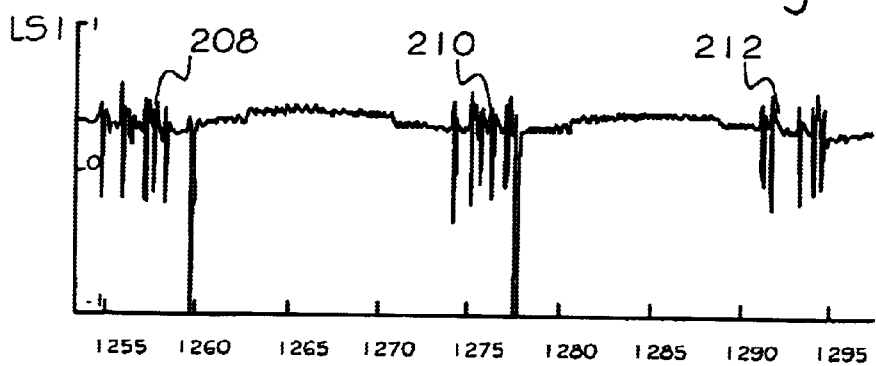

FIGS. 10a, 10b and 10c illustrate the relation between the electrical activity of a rabbit uterus, the intra uterine pressure and the timing of an inhibitory UCM trapezoidal signal with respect to a uterine contraction. All figures correlate sharing the same time scale (the X axis). FIG. 10b shows a plot of a rabbit's intrauterine pressure readings against time, FIG. 10c shows a plot of the electrical activity of the uterus with respect to time and FIG. 10a shows inhibitory UCM trapezoidal signals applied on the rabbit's uterus with respect to time Each inhibitory UCM trapezoidal signal (200, 202) is applied upon detection of a uterine contraction (204, 206 corresponding to electrical activity fluctuation readings 208, 210—electrical activity fluctuation 212 corresponding to a third contraction 208). Trapezoidal UCM signal brings about certain advantages. A trapezoidal signal-application duration may be longer than the application duration of a square UCM signal, without risking depolarization effects and with reduced desensitization associated with a square signal, due to the gradual energy decrease. Trapezoidal UCM signal sequence requires less energy than corresponding square UCM signal sequence. It is again noted that although the drop of signal intensity is linear in FIG. 10a, the drop may also be non-linear.

Figure 11:
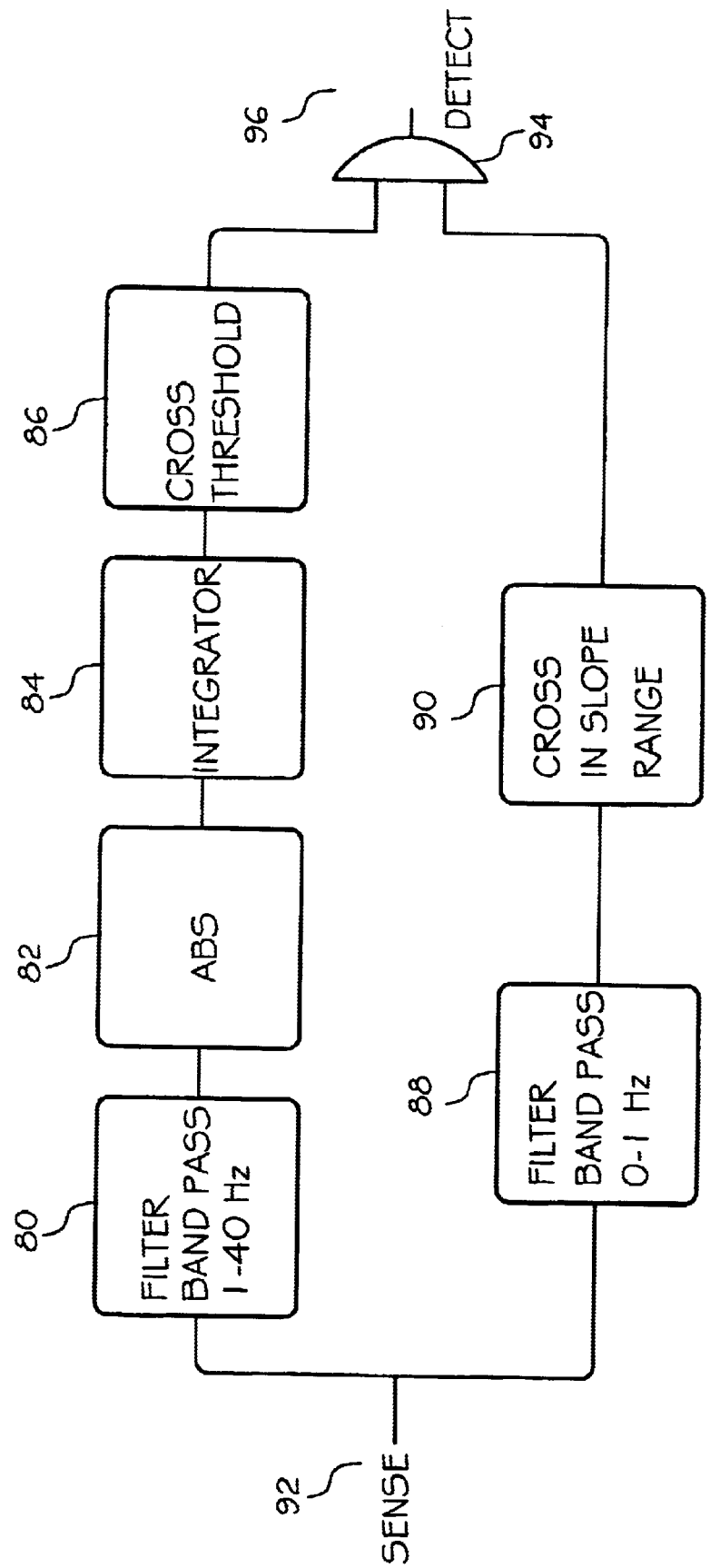
FIG. 11 illustrates an algorithm for detecting spontaneous contractions of the uterus.

FIG. 11 illustrates an algorithm for detecting spontaneous contractions of the uterus.

The control unit may be adapted to use a predefined algorithm to detect an event of spontaneous contraction in order to initiate a UCM signal. An event (occurrence of a spontaneous contraction) may be defined as crossing a predetermined threshold of pressure or strain or electrical activity of the uterus. An alternative definition may be the combination of crossing that predetermined threshold in a predetermined range of slopes (of the contraction curve). It is known that electrical activity associated with uterine contraction has two distinct characteristics: rapid AC activity in the range of 1 to 40 Hz, as well as pulsed activity in the range of 0–1.

A sensed electrical signal (detecting contractions) is split to pass through filter 80 with band pas of 1–40 Hz, followed by ABS 82 (absolute value), integrator (84) and finally it is determined whether the predetermined threshold was passed 86. Parallel to that the same sensed signal is passed through filter 99 with band pass of 0–1 Hz and then it is determined whether the signal slope is within the predetermined range 90. An AND logic element determines that both parameters are met to produce a detect signal Each of these parameters may be solely considered as indicating contraction, but the combination of both parameters may increase the detection reliability.

It should be noted that various embodiments of the present invention as described herein might be used in conjunction with drug therapies, with a synergistic interaction and/or to allow a reduced dose of drug to produce a desired effect and/or to allow increased dosages of drugs to be used, while limiting their adverse side effects using electrical control.

UCM enhancing signals may be used to induce labor in overdue pregnancies, as well as inducing labor much earlier to terminate undesired pregnancy (abortion).

UCM enhancing signals may be applied for the purpose of initiating labor, initiating labor favorable conditions (for example enhance the generation of gap junctions, or even initiate gap junctions).

Another application of UCM treatment is related to miscarriage. It is believed that miscarriage may be a result of weak cervix. Sometimes cervical cerclage (stitching of the cervix to prevent premature opening) is needed to prevent the cervix from giving in to the weight of the fetus (cervical incompetence). It is known that the cervix comprises mostly collagen and 10–20% of muscles. UCM treatment (presumably strong contracting signal) applied on the cervix may result in strengthening of the cervix.

The UCM waveforms may have different shapes—examples include rectangular wave or other waveforms such as described in PCT/IL97/00243. It is also suggested to apply superposed AC wave pattern on a DC wave patern, such as for example 5–100 Hz AC wave superposed on a rectangular DC wave.

The uterus control device of the present invention may be used for more applications, some of which are given herein for example, without derogating generality.

IVF (In Vitro Fertilization) pregnancies are growing in numbers as IVF techniques improve and become more efficient and successful. It is estimated that some 10–15% of all pregnancies in the US are IVF pregnancies. It is known that in some cases of women undergoing IVF treatment the existence of uterine contractions over a certain threshold (baseline) prevents successful implantation of the fetus and hence results in failure. In order to reduce the risk of failed implantation it is known that attempts were made to keep the uterus quiescent by administering medications such as ritodrine or perform other pharmaceutical interventions. It is suggested to use the uterus controller of the present invention to lower the contraction baseline of women undergoing IVF treatment and who experience strong contractions that threaten the successful completion of IVF treatment. The uterus controller is to be used to deliver inhibiting signals in order to reduce the level of uterine contractions bellow the initial undesirable baseline. Again it is noted that UCM is not dangerous to the mother or the fetus, and is far more favorable than pharmaceutical intervention.

Another application of UCM deals with amniocentesis and chorionic villus sampling. Amniocentesis and chorionic villus sampling are widely performed procedures in obstetrics, used to diagnose fetal hereditary diseases. As the process of deciphering the human genetic code advances these procedures become increasingly more important. It is estimated that a risk of about 0.5–5% of loosing the fetus is involved in these procedures, mainly due to uterine stimulation caused by puncturing of the amnion membrane. By performing UCM in accordance with the present invention these stimulated contractions may be inhibited thus greatly reducing the risk involved in amniocentesis and chorionic villus sampling. In a preferred embodiment of the present invention women undergoing amniocentesis or chorionic villus sampling procedures will be connected to the UCM device for a predetermined period of time during and after the procedure (for example for a period of 48 hours after the procedure has been performed, that is considered to be the crucial period during which stimulated contractions may appear). Commonly doctors prescribe women undergoing these procedures rest in bed after the performance of the procedure and recommend 1–3 days of leave from work. The use of UCM is therefore not only beneficial from health considerations but also financially desirable.

Yet another application of UCM treatment is related to multiple fetus pregnancies. Multiple fetus pregnancies occur spontaneously in some pregnancies but substantially in pregnancies resulting from IVF or other forms of fertility treatment. The risk of preterm in multiple fetus pregnancies is statistically much greater than in single fetus pregnancies. By applying UCM treatment such premature delivery may be contained and prevented, employing the UCM inhibiting signal. As a result many complications due to preterm delivery may be reduced or eliminated.

Still another possible application of UCM treatment relates to fetal surgery Fetal surgery performed on a fetus while still growing in the womb is a relatively new surgical field, currently mainly dealing with diaphragmatic hernia repair, urinary anomalies etc. To date fetal surgery involves exceptionally high incidence rate of preterm labor (up to 50%!) and that is considered as a serious drawback obstructing further development of fetal surgery. It is stipulated that applying UCM treatment on pregnant women whose fetus undergoes surgery would inhibit undesirable stimulated labor and contain it, greatly reducing preterm labor in fetal surgery cases.

Yet another possible application of UCM treatment relates to abdominal operations in pregnant women. Abdominal surgery in pregnant women is preferably avoided and performed only in emergencies like appendicitis, cholecystitis, trauma cases etc. It is estimated that about 2–5 in 1000 pregnant women in the US have to undergo emergency surgery during their pregnancy The risk of preterm labor in these operations is high. It is recommended to perform inhibiting UCM treatment in these cases to contain uterine contractions and thus greatly reduce the risk of preterm labor.

It should be clear that the description of the embodiments and attached Figures set forth in this specification serves only for a better understanding of the invention, without limiting its scope as covered by the appending claims.

It should also be clear that a person skilled in the art, after reading the present specification could make adjustments or amendments to the attached Figures and above described embodiments but these would still be covered by the appending claims.

What is claimed is:

1. A method for controlling contractions of a uterus of a female comprising:

providing at least one of a plurality of sensors for sensing uterine contractions;

providing an electric signal generator for generating electric signals to be applied on the uterus;

providing a control unit adapted to receive a signal corresponding to a sensed uterine contraction from said at least one of a plurality of sensors and actuate said signal generator to generate a non-excitatory electric signal in a predetermined timing and duration with respect to the sensed uterine contraction;

providing electric signal delivery means for the delivering electric signal from the electric signal generator to at least one of a plurality of predetermined locations on the uterus;

sensing a uterine contraction using said at least one of a plurality of sensors; and applying non-excitatory electric field at said at least one of a plurality of predetermined locations on the uterus in predetermined timing and duration with respect to the sensed uterine contraction.

2. A method for enhancing contractions of a uterus of a female comprising:

providing at least one of a plurality of sensors for sensing uterine contractions;

providing an electric signal generator for generating electric signals to be applied on the uterus;

providing a control unit adapted to receive the signal corresponding to a uterine contraction from said at least one of a plurality of sensors and actuate said signal generator to generate a non-excitatory electric signal in a predetermined timing and duration with respect to the sensed uterine contraction;

providing electric signal delivery means for the delivery of electric signal from the electric signal generator to at least one of a plurality of predetermined locations on the uterus;

sensing a uterine contraction using said at least one of a plurality of sensors; and applying non-excitatory electric field at said at least one of a plurality of predetermined locations on the uterus in a predetermined timing and duration with respect to the sensed uterine contraction.

3. A method for controlling contractions of a uterus of a female comprising:

providing at least one of a plurality of sensors adapted to sense uterine contractions;

providing an electric signal generator for generating electric signals to be applied on the uterus;

providing a control unit adapted to receive the signal corresponding to a uterine contraction from said at least one of a plurality of sensors and actuate said signal generator to generate a non-excitatory electric signal in a predetermined timing and duration with respect to the sensed uterine contraction;

providing electric signal delivery means for delivering electric signal from the electric signal generator to at least one of a plurality of predetermined locations on the uterus;

sensing a uterine contraction using said at least one of a plurality of sensors; and applying non-excitatory electric field at said at least one of a plurality of predetermined locations on the uterus in a predetermined timing and duration with respect to the sensed uterine contraction, said electric field commencing not before commencement of the uterine contraction.

4. The method of claim 3, wherein it is used for enhancing uterine contractions, and wherein the non-excitatory electric field is terminated not later than the end of a peaked substantially plateau level in said contraction.

5. The method of claim 4, wherein said at least one of a plurality of sensors is a sensing electrode and wherein commencement of the contraction is determined by commencement of erratic electric activity of the uterus sensed by the sensing electrode and the end of a plateau level in said contraction is determined by termination of the erratic electric activity.

6. The method of claim 4, wherein said at least one of a plurality of sensors is an intra-uterine pressure sensor and wherein commencement of the contraction is determined by commencement of rise in pressure activity of the uterus sensed by the intra-uterine pressure sensor and the end of a plateau level in said contraction is determined by a drop in the intra-uterine pressure level following the peaked substantially plateau level.

7. The method of claim 4 wherein the duration of the applied non-excitatory electric field is not greater than about 10 percent of the duration of a contraction cycle.

8. The method of claim 3 wherein the non-excitatory electric field is applied with a delay after the commencement of the uterine contraction.

9. The method of claim 3 wherein the non-excitatory electric field comprises a substantially constant non-excitatory electric field.

10. The method of claim 9 wherein the substantially constant non-excitatory electric field is stopped before anticipated commencement of a uterine contraction.

11. The method of claim 3, wherein said electric field has a square waveform.

12. The method of claim 3, wherein said electric field has a trapezoidal waveform.

13. The method of claim 3, wherein said electric field ends in a gradual drop.

14. The method of claim 13, wherein the gradual drop is linear.

15. The method of claim 13, wherein the gradual drop is non-linear.

16. The method of claim 13, wherein the gradual drop is exponential.

17. The method of claim 13, wherein the gradual drop is hyperbolic.

18. The method of claim 3 wherein said plurality of sensors comprise sensing electrodes for measuring electromyography (EMG) signals.

19. The method of claim 5 wherein in order to synchronize output waves to uterine contractions at least one of said plurality of sensors is placed on the abdomen of the female.

20. The method of claim 3 wherein said plurality of sensors comprise intra-uterine pressure sensors.

21. The method of claim 3 wherein said plurality of sensors comprise mechanical sensors.

22. The method of claim 21 wherein said mechanical sensors comprise strain gauge sensors.

23. The method of claim 22 wherein said strain gauge sensors are placed on the abdomen of the female.

24. The method of claim 3 wherein said at least one of a plurality of sensors is inserted vaginally and placed in contact with the cervix of the uterus.

25. The method of claim 3 wherein said electric signal delivery means comprise at least one of a plurality of electrodes.

26. The method of claim 25 wherein said electrodes are selected from stitch electrodes, patch electrodes, net-like electrodes.

27. The method of claim 25 wherein said electrodes are deployed transcutanouesly.

28. The method of claim 25 wherein said electrodes are deployed vaginally.

29. The method of claim 25 wherein said at least one of a plurality of electrodes is placed in vicinity to the fundus of the uterus.

30. The method of claim 3 wherein said control unit continuously samples sensed signal from said at least one of a plurality of sensors and estimates the timing of initiation of said sensed contractions, the magnitude of said sensed contractions, and the rhythm of said contractions, whereby the magnitude of the contractions, and the rhythm of sensed contractions are used to estimate progression of labor in time to determine a necessity for any electrical intervention or determine the need to terminate the therapy.

31. The method of claim 30 wherein said non-excitatory electric field is applied in synchrony with the sensed uterine contractions.

32. The method of claim 3 wherein said control unit is programmable.

33. The method of claim 32 wherein said control unit is a PC.

34. The method of claim 4 wherein the non-excitatory electric field is applied in duration in the range of 100 milliseconds to 5 seconds.

35. The method of claim 3, wherein the non-excitatory electric field strength is in the range of 500 microamperes to 20 milliamperes.

36. The method of claim 35 wherein the non-excitatory electric field strength is in the range of 2 to 6 milliamperes.

37. The method of claim 3 used for slowing the rhythm of contractions but substantially retaining the amplitude of contractions, wherein the non-excitatory electric field duration is in the range of 6 to 10 seconds.

38. The method of claim 3 used for inhibiting uterine contractions, wherein the non-excitatory electric field is in the range of 10 seconds to 100 seconds.

39. The method of claim 3 applied in conjunction with drug therapy.

40. A device for controlling contractions of a uterus of a female comprising:

at least one of a plurality of sensors for sensing uterine contractions;

an electric signal generator for generating electric signals to be applied on the uterus;

electric signal delivery means for delivering electric signal from the electric signal generator to at least one of a plurality of predetermined locations on the uterus; and a control unit for receiving signals corresponding to uterine contractions from said sensors and actuate said signal generator in a predetermined manner for generating non-excitatory electric field at said at least one of a plurality of predetermined locations on the uterus in predetermined timing and duration with respect to the sensed uterine contraction.

41. The device of claim 40, wherein said electric signal generator generates a substantially constant non-excitatory electric field.

42. The device of claim 41 wherein said electric signal generator is occasionally switches the polarity of said non-excitatory electric field so as to reduce ionic polarization effects.

43. The device of claim 41, wherein said electric signal generator stops said substantially constant non-excitatory electric field before anticipated commencement of a uterine contraction.

44. The device of claim 40 designed for inhibiting uterine contractions, wherein the electric signal generator generates a non-excitatory electric field in the range of 10 seconds to 100 seconds.

45. The device of claim 41 wherein the electric signal generator applies said non-excitatory electric field with a time delay with respect to commencement of a uterine contraction.

46. The device of claim 40, wherein said plurality of sensors comprise sensing electrodes for measuring electromiography EMG signals.

47. The device of claim 40, wherein at least one of said plurality of sensors is adapted to be placed on the abdomen of the female in order to synchronize output waves to spontaneous uterine contractions.

48. The device of claim 40, wherein said plurality of sensors comprise intra-uterine pressure sensors.

49. The device of claim 40, wherein said plurality of sensors comprise mechanical sensors.

50. The device of claim 49 wherein said mechanical sensors comprise strain gauge sensors.

51. The device of claim 50 wherein said strain gauge sensors are adapted to be placed on the abdomen of the female.

52. The device of claim 40 wherein said at least one of a plurality of sensors is adapted to be inserted vaginally and placed in contact with the cervix of the uterus.

53. The device of claim 40, wherein said electric signal delivery means comprise at least one of a plurality of electrodes.

54. The device of claim 53 wherein said electrodes are selected from stitch electrodes, patch electrodes, net-like electrodes.

55. The device of claim 53 wherein said electrodes are deployable transcutanouesly.

56. The device of claim 53 wherein said electrodes are deployable vaginally.

57. The device of claim 53 wherein said at least one of a plurality of electrodes is to be placed in the vicinity of the fundus of the uterus.

58. The device of claim 40 wherein said control unit continuously samples said at least one of a plurality of sensors input and estimates the timing of initiation of said sensed contractions, the magnitude of said sensed contractions, and the rhythm of said contractions, whereby the magnitude of the contractions, and the rhythm of contractions are used to estimate progression of labor in time to determine a necessity for any electrical intervention or determine the need to stop therapy.

59. The device of claim 40 wherein said control unit is programmable.

60. The device of claim 59 wherein said control unit is a PC.

61. The device of claim 40, wherein said electric signal generator generates electric field having a square waveform.

62. The device of claim 40, wherein said electric signal generator generates electric field having a trapezoidal waveform.

63. The device of claim 40, wherein said electric signal generator generates electric field that ends in a gradual drop.

64. The device of claim 63, wherein the gradual drop is linear.

65. The device of claim 63, wherein the gradual drop is non-linear.

66. The device of claim 63, wherein the gradual drop is exponential.

67. The device of claim 63, wherein the gradual drop is hyperbolic.

68. The device of claim 40 wherein the electric signal generator generates a non-excitatory electric field having a duration in the range of 100 milliseconds to 5 seconds.

69. The device of claim 40 wherein the electric signal generator generates a non-excitatory electric field of a strength in the range of 500 microamperes to 20 milliamperes.

70. The device of claim 69 wherein the electric signal generator generates a non-excitatory electric field of a strength in the of 2 to 6 milliamperes.

71. The device of claim 40 designed for slowing the rhythm of contractions but substantially retaining the amplitude of contractions, wherein the electric signal generator generates a non-excitatory electric field with duration in the range of 6 to 10 seconds.

* * * * *